United States Patent [19]

Gitlis

[11] Patent Number: 4,616,939
[45] Date of Patent: Oct. 14, 1986

[54] APPARATUS FOR TESTING DIAMONDS

[76] Inventor: Meir Gitlis, Moshav Bnei Atarot, Israel

[21] Appl. No.: 610,353

[22] Filed: May 15, 1984

[51] Int. Cl.$^4$ .......................................... G01N 25/18
[52] U.S. Cl. ..................................................... 374/44
[58] Field of Search ...................... 374/43, 44, 29, 178

[56] References Cited

U.S. PATENT DOCUMENTS

| | | | |
|---|---|---|---|
| 3,611,786 | 10/1971 | Schorr | 374/44 |
| 4,090,151 | 5/1978 | Presset et al. | 374/178 |
| 4,137,770 | 2/1979 | Trout | 374/178 |
| 4,255,962 | 3/1981 | Ashman | 374/44 |
| 4,344,315 | 8/1982 | Moxon et al. | 374/44 |
| 4,364,677 | 12/1982 | Ashman | 374/44 |
| 4,395,139 | 7/1983 | Namiki et al. | 374/178 |

OTHER PUBLICATIONS

National Semiconductor Linear Data Book, 1976, National Semiconductor, Santa Clara, Ca., pp 2-22-2-24.

Primary Examiner—Charles Frankfort
Assistant Examiner—Thomas B. Will
Attorney, Agent, or Firm—Panitch Schwarze Jacobs and Nadel

[57] ABSTRACT

Apparatus for testing diamonds for genuineness including a housing, a probe tip mounted in the housing and formed of a conductive material, a voltage stabilizer located in the housing remote from the probe and coupled to the probe tip by conductive material, the voltage stabilizer being operative to provide an output voltage which varies as a function of the temperature of the conductive probe tip, and indicating apparatus operative to provide a sensible output indication of genuineness of a diamond in response to the output voltage from the voltage stabilizer.

5 Claims, 3 Drawing Figures

APPARATUS FOR TESTING DIAMONDS

FIELD OF THE INVENTION

The present invention relates to testing apparatus and more particularly to testing apparatus for crystalline articles, such as diamonds.

BACKGROUND OF THE INVENTION

Various types of testers for crystalline substances are known in the prior art and in the patent literature. These include apparatus for determining the genuineness of diamonds employing conductivity measurements. Such apparatus is exemplified in U.S. Pat. Nos. 4,255,962; 4,364,677; and 4,344,315 all of which employ temperature sensitive elements, such as thermistors, located at the tip of a probe, which tip is firmly contacted with a diamond to be tested. The thermistors measure the thermal response of the probe tip. Devices of the type described in the aforesaid U.S. Patents are relatively expensive, sensitive and complex electronically.

SUMMARY OF THE INVENTION

The present invention seeks to provide an improved diamond testing device which is significantly less complex and expensive than the prior art devices described hereinabove.

There is thus provided in accordance with an embodiment of the present invention apparatus for testing diamonds for genuineness comprising a housing, a probe tip mounted in the housing and formed of a conductive material, a voltage stabilizer located in the housing remote from the probe and coupled to the probe tip by conductive material, the voltage stabilizer being operative to provide an output voltage which varies as a function of the temperature of the conductive probe tip, and indicating apparatus operative to provide a sensible output indication of genuineness of a diamond in response to the output voltage from the voltage stabilizer.

Further in accordance with an embodiment of the present invention there is also included in the diamond testing apparatus, a device for sensing the pressure of the probe tip on the substance being tested and apparatus for calibrating the sensed conductivity of the substance being tested in accordance with the sensed pressure.

Additionally in accordance with a preferred embodiment of the present invention, the voltage stabilizer comprises a precision temperature stabilized zener diode.

Further in accordance with a preferred embodiment of the invention, the precision temperature stabilized zener diode LM 399A manufactured by National Semiconductor.

BRIEF DESCRIPTION OF THE DRAWINGS

The present invention will be understood and appreciated more fully from the following detailed description taken in conjunction with the drawings in which.

DETAILED DESCRIPTION OF THE INVENTION

Figure 1:
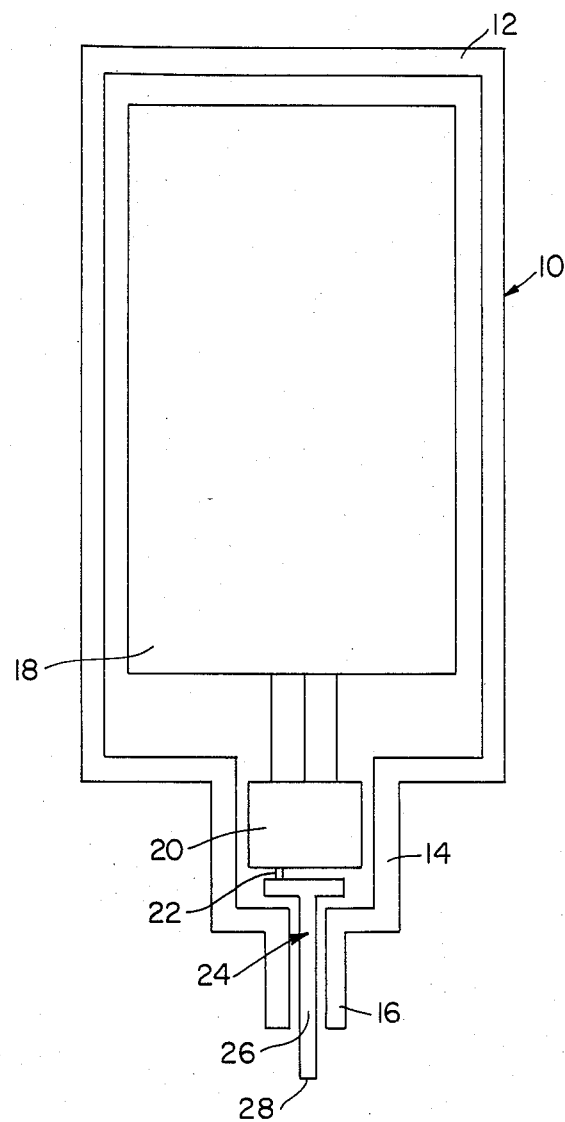
FIG. 1 is a schematic illustration of testing apparatus constructed and operative in accordance with an embodiment of the present invention.

Reference is now made to FIG. 1 which illustrates testing apparatus suitable for conductivity testing of the genuineness of diamonds and comprising a housing 10 defining a body portion 12, a grip portion 14 and a tip portion 16. Disposed in body portion 12 of the housing 10 is test circuitry 18, which will be described hereinafter in greater detail with reference to FIG. 2.

Disposed within the grip portion 14 of the housing 10 and electrically coupled to circuitry 18 is a thermal sensor 20, which according to a preferred embodiment of the invention comprises a precision temperature-stabilized monolithic zener diode, such as an LM399. The LM399 is preferred because it operates at an elevated temperature and provides a highly precise voltage change in response to temperature losses produced by contact with a highly conductive element such as a genuine diamond. Thermally coupled to the thermal sensor 20, as by a good thermal conductor 22, is a probe element 24, typically formed of copper or any other suitable conductor, which includes an elongate portion 26 which extends through the tip portion 16 of the housing 10 and defines at its extreme end, a contact tip 28 for engagement with a substance to be tested.

Figure 2:
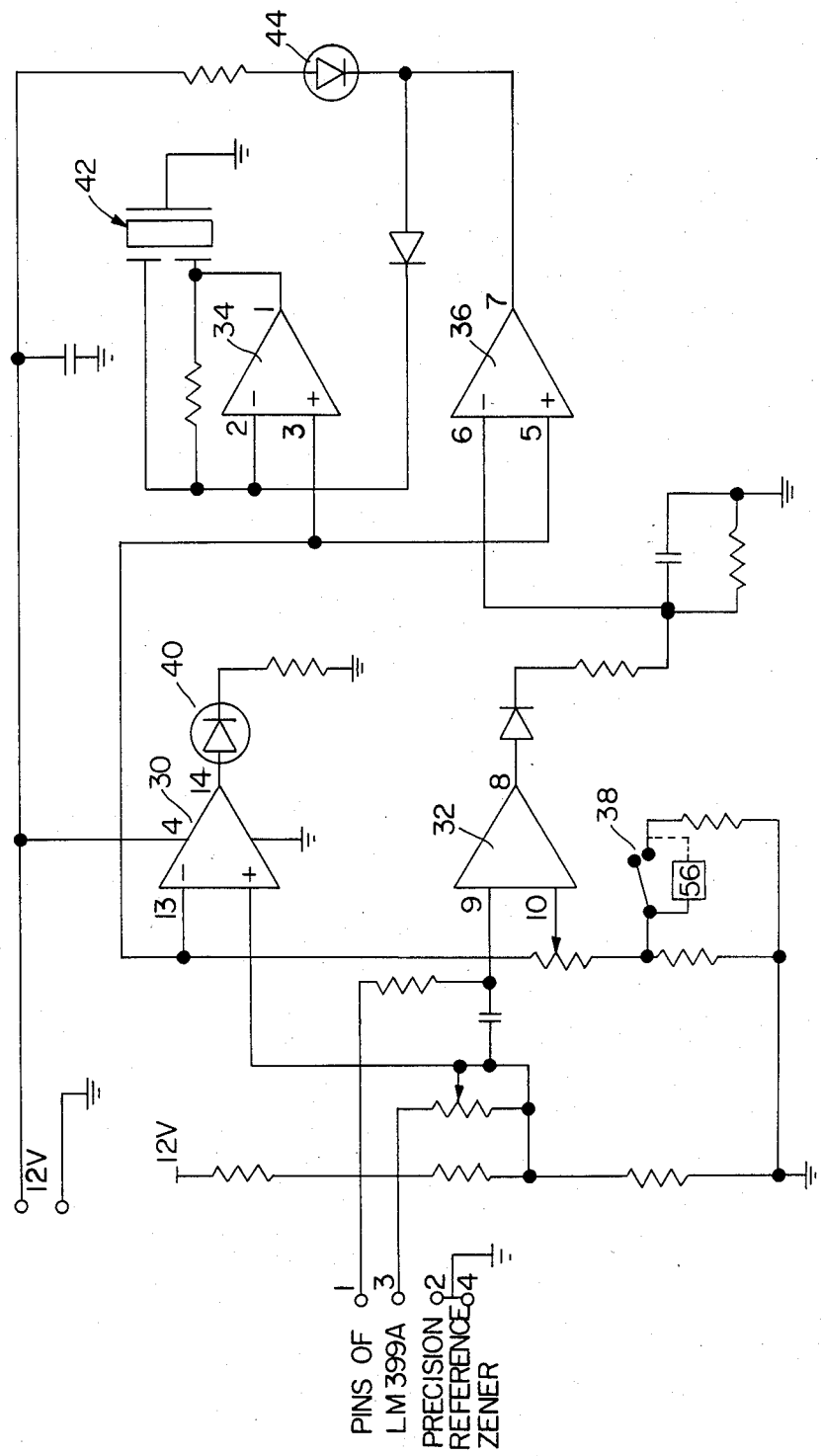
FIG. 2 is a circuit diagram illustrating the circuitry employed in a preferred embodiment of the testing apparatus of FIG. 1.

Reference is now made to FIG. 2 which is a circuit diagram of a preferred embodiment of testing circuit useful in the apparatus of FIG. 1. The circuit is based on four operational amplifiers 30, 32, 34, and 36 which are conveniently embodied in a single integrated circuit, such as a 324 of National Semiconductor. Briefly stated, the testing circuit is arranged to sense the conductivity of the subject substance being tested. When the contact tip 28 of the probe element 24 contacts a good heat conductor such as a diamond, the temperature of the thermal sensor 20 drops and the output voltage of the thermal sensor 20 changes. Because the thermal sensor 20 is temperature-stabilized by action of a heater contained within the thermal sensor 20, the change in the temperature of the thermal sensor 20 caused by the contact of the probe element 24 with the diamond turns on a heater contained within the thermal sensor 20. Eventually, the heater increases the temperature of the thermal sensor 20, restoring the voltage output of the thermal sensor 20 to its initial level. However, in the interim, the contact of the contact lip 28 with a heat conductor causes a voltage transient in the output of the thermal sensor 20. A good heat conductor such as a diamond produces a relatively large voltage transient. The magnitude of this transient is compared by the circuitry 18 with a reference voltage, and if the voltage transient is sufficiently great, indicating that the object tested has the thermal conductivity of a genuine diamond, the circuitry 18 gives a sensible indication of this fact. In order to take into account the size of the mass of the substance being tested, there is provided a switch 38 for adding additional resistance to the circuit when the switch is closed, in order to accurately test relatively large mass substances, such as large diamonds of the order of 0.15 carat or more.

An LED 40 is provided at the output of operational amplifier 30 and is operative to illuminate when the temperature at the probe element 26 is at a predetermined desired initial temperature suitable for beginning testing.

A piezoelectric crystal sound transducer 42, which is commercially available from Phillips of the Netherlands, is provided along a feedback loop between the output of operational amplifier 34 and the negative input thereto and is operative to provide an audio output when a genuine diamond is tested. An LED 44 is also coupled to the negative input of operational amplifier 34 and is operative to illuminate in response to the sensing of a genuine diamond by the testing circuit.

Both the constructional principles of the testing circuit and the criteria for determining what conductivity is indicative of a genuine diamond are well known in the prior art, inter alia from the prior art patents described hereinabove. Operational amplifier 30 is operative to illuminate LED 40 when the thermal sensor 20 reaches a predetermined temperature which is suitable for testing. Operational amplifier 32 functions as a comparator to determine the threshold at which conductivity of a genuine diamond activates the device. Operational amplifier 36 functions in response to the output of the operational amplifier 32 to illuminate LED 44 in the sensed presence of a genuine diamond. Operational amplifier 34 is operative to cause activation of the transducer 42 in response to the output of operational amplifier 36.

Switch 38 is operative to vary the resistance of the reference of operational amplifier 32 by selectively switching additional resistance into and out of the circuit.

Calibration of the testing circuitry is achieved empirically by adjusting the potentiometer at the output 10 to operational amplifier 32.

Figure 3:
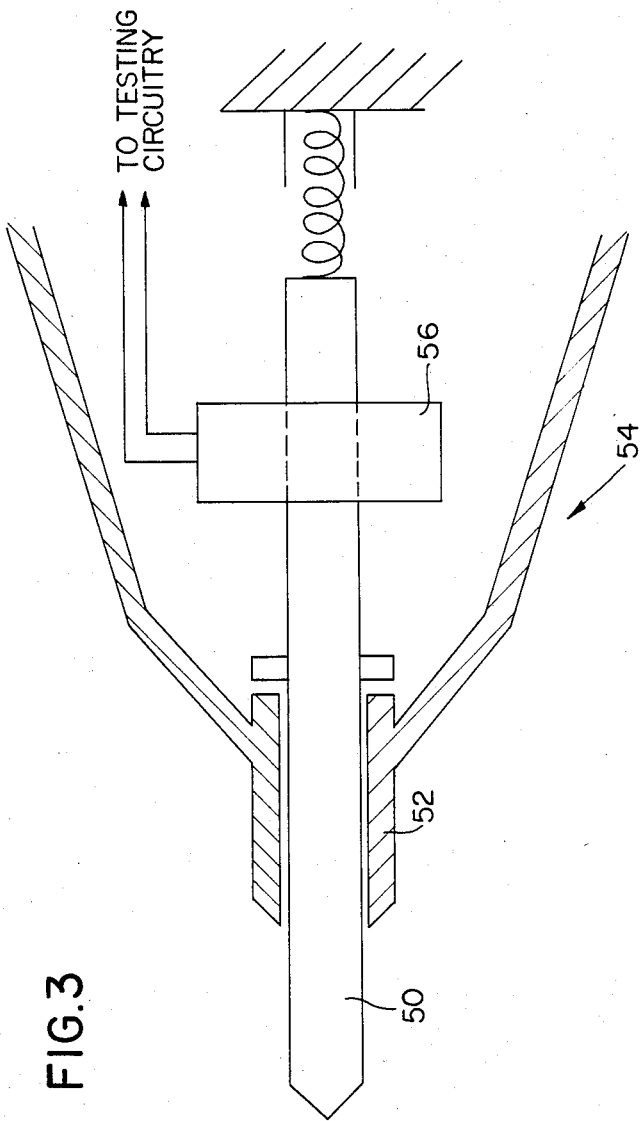
FIG. 3 is a schematic illustration of the probe portion of modified testing apparatus constructed and operative in accordance with an alternative embodiment of the present invention.

Reference is now made to FIG. 3 which illustrates the probe construction of an alternative embodiment of the invention. Here a tip element 50 is spring mounted for axial movement with respect to the tip portion 52 of a housing 54. A strain gauge 56 is connected along tip element 50 for sensing the amount of force exerted thereon. The output indication of the strain gauge or of any other suitable force measuring means is supplied to the testing circuitry and is used to calibrate the testing circuitry according to the applied force between the tip and the substance being tested, since the measured conductivity is a function of this applied force.

In the embodiment of FIG. 2, the strain gage 56 of FIG. 3 may be connected in parallel with switch 38 as shown in FIG. 2. Strain gage 56 is operative to vary the reference resistance at input 10 of operational amplifier 32 as a function of the pressure exerted on the tip. In this manner, compensation is provided for differences in the pressure applied by various users, since the measured conductivity varies somewhat as a function of the pressure of the tip applied to the substance being tested.

It will be appreciated by persons skilled in the art that the present invention is not limited by what has been particularly shown and described hereinabove. Rather the scope of the present invention is defined only by the claims which follow:

I claim:

1. Apparatus for testing diamonds for genuineness by sensing the thermal conductivity of a substance tested comprising:
    a housing;
    a probe tip mounted in said housing and formed of a conductive material;
    a voltage stabilizer located in said housing remote from said probe tip and coupled to the probe tip by a conductor, said voltage stabilizer being operative to provide an output voltage which varies as a function of the temperature of the conductive probe tip;
    indicating apparatus operative to provide a sensible output indication of genuineness of said diamonds in response to the output voltage from the voltage stabilizer; and
    means for sensing the pressure of the probe tip on the substance being tested and apparatus for calibrating the sensed conductivity of the substance being tested in accordance with the sensed pressure.

2. Apparatus according to claim 1 and wherein said voltage stabilizer comprises a precision temperature stabilized zener diode.

3. Apparatus according to claim 1 and also including audio indicating means for indicating the genuineness of a diamond being tested.

4. Apparatus according to claim 1 and wherein said indicating apparatus also comprises variable resistance switching means associated with said voltage stabilizer for adapting testing to different masses of diamonds to be tested.

5. Apparatus according to claim 1 and also comprising means for providing a visible output indication of a genuine diamond being tested.

* * * * *